United States Patent
Levin

(10) Patent No.: US 10,040,735 B2
(45) Date of Patent: Aug. 7, 2018

(54) METHOD OF PRODUCING AN ALCOHOL-CONTAINING PYROLISIS PRODUCT

(71) Applicant: Doron Levin, Highland Park, NJ (US)

(72) Inventor: Doron Levin, Highland Park, NJ (US)

(73) Assignee: EXXONMOBIL RESEARCH AND ENGINEERING COMPANY, Annandale, NJ (US)

( * ) Notice: Subject to any disclaimer, the term of this patent is extended or adjusted under 35 U.S.C. 154(b) by 267 days.

(21) Appl. No.: 14/696,688

(22) Filed: Apr. 27, 2015

(65) Prior Publication Data

US 2015/0321980 A1    Nov. 12, 2015

Related U.S. Application Data

(60) Provisional application No. 61/990,182, filed on May 8, 2014.

(51) Int. Cl.
| | | |
|---|---|---|
| *C07C 29/141* | (2006.01) | |
| *C10B 49/22* | (2006.01) | |
| *C10B 53/02* | (2006.01) | |
| *C10B 57/06* | (2006.01) | |
| *C10G 3/00* | (2006.01) | |

(Continued)

(52) U.S. Cl.
CPC ............ *C07C 29/141* (2013.01); *C10B 49/22* (2013.01); *C10B 53/02* (2013.01); *C10B 57/06* (2013.01); *C10G 3/45* (2013.01); *C10G 3/47* (2013.01); *C10G 3/48* (2013.01); *C10G 3/50* (2013.01); *B01J 23/58* (2013.01); *B01J 23/63* (2013.01); *B01J 23/78* (2013.01);

(Continued)

(58) Field of Classification Search
CPC ....... C07C 29/141; C10B 49/22; C10B 53/02; C10B 57/06; C10G 3/45; C10G 3/47; C10G 3/48; C10G 3/50; C10G 2300/1014; B01J 23/58; B01J 23/63; B01J 23/78; Y02E 50/14; Y02P 20/145; Y02P 30/20

See application file for complete search history.

(56) References Cited

U.S. PATENT DOCUMENTS

| 3,539,306 A | 11/1970 | Kumura et al. |
| 4,656,156 A | 4/1987 | Misra |

(Continued)

FOREIGN PATENT DOCUMENTS

WO    WO2014023758 A2    2/2014

OTHER PUBLICATIONS

S. Cannizzaro, On benzoic acid-equivalent alcohol, Letter Communication, undated, pp. 129-130.

(Continued)

*Primary Examiner* — Medhanit W Bahta
(74) *Attorney, Agent, or Firm* — Andrew T. Ward; Amanda K. Jenkins

(57) ABSTRACT

Methods are provided for producing an alcohol-containing pyrolysis product. Initially, a hydrocarbon feedstock is pyrolyzed in the presence of a catalyst system, the catalyst system comprising a basic metal oxide catalyst and a hydrogenation metal catalyst. A pyrolysis product is produced that contains at least one alcohol. The basic metal oxide catalyst is comprised of at least one metal from Group 2, Group 3 including Lanthanides and Actinides, or Group 4 of the Periodic Table of Elements, and the supported hydrogenation metal catalyst is comprised of at least one metal from Group 6 or Groups 8-10 of the Periodic Table of Elements.

7 Claims, 1 Drawing Sheet

(51) Int. Cl.
  *B01J 23/58* (2006.01)
  *B01J 23/63* (2006.01)
  *B01J 23/78* (2006.01)
(52) U.S. Cl.
  CPC ...... *C10G 2300/1014* (2013.01); *Y02E 50/14* (2013.01); *Y02P 20/145* (2015.11); *Y02P 30/20* (2015.11)

(56) References Cited

U.S. PATENT DOCUMENTS

| | | | |
|---|---|---|---|
| 4,883,533 A | 11/1989 | Kosin et al. | |
| 4,904,457 A | 2/1990 | Misra | |
| 5,364,828 A | 11/1994 | Cox et al. | |
| 6,844,291 B2 | 1/2005 | Levin et al. | |
| 6,951,830 B2 | 10/2005 | Janssen | |
| 6,995,111 B2 | 2/2006 | Levin et al. | |
| 7,199,278 B2 | 4/2007 | Fung et al. | |
| 7,220,352 B2 | 5/2007 | Halbert et al. | |
| 7,244,352 B2 | 7/2007 | Halbert et al. | |
| 7,288,181 B2 | 10/2007 | Shih et al. | |
| 7,288,182 B1 | 10/2007 | Soled et al. | |
| 7,307,196 B2 | 12/2007 | Levin et al. | |
| 7,319,178 B2 | 1/2008 | Levin et al. | |
| 7,378,563 B2 | 5/2008 | Levin et al. | |
| 7,411,106 B2 | 8/2008 | Xu et al. | |
| 7,435,335 B1 | 10/2008 | Ellis et al. | |
| 7,468,465 B2 | 12/2008 | Vartuli et al. | |
| 7,513,989 B1 | 4/2009 | Soled et al. | |
| 8,202,332 B2 | 6/2012 | Agblevor | |
| 8,293,952 B2 | 10/2012 | Levin | |
| 2009/0151253 A1 | 6/2009 | Manzer et al. | |
| 2011/0232166 A1 | 9/2011 | Kocal | |
| 2011/0245545 A1 | 10/2011 | Levin | |

OTHER PUBLICATIONS

O.B. Koper, I. Lagadic, A. Volodin and K.J. Klabunde, "Alkaline-Earth Oxide Nanoparticles Obtained by Aerogel Methods. Characterization and Rational for Unexpectedly High Surface Chemical Reactivities", Chem. Mater., 1997, 9, pp. 2468-2480.

PCT Application No. PCT/US2015/027892, Communication from the International Searching Authority, Forms PCT/ISA/220, PCT/ISA/210 and PCT/ISA/237, dated Sep. 22, 2015, 15 pages.

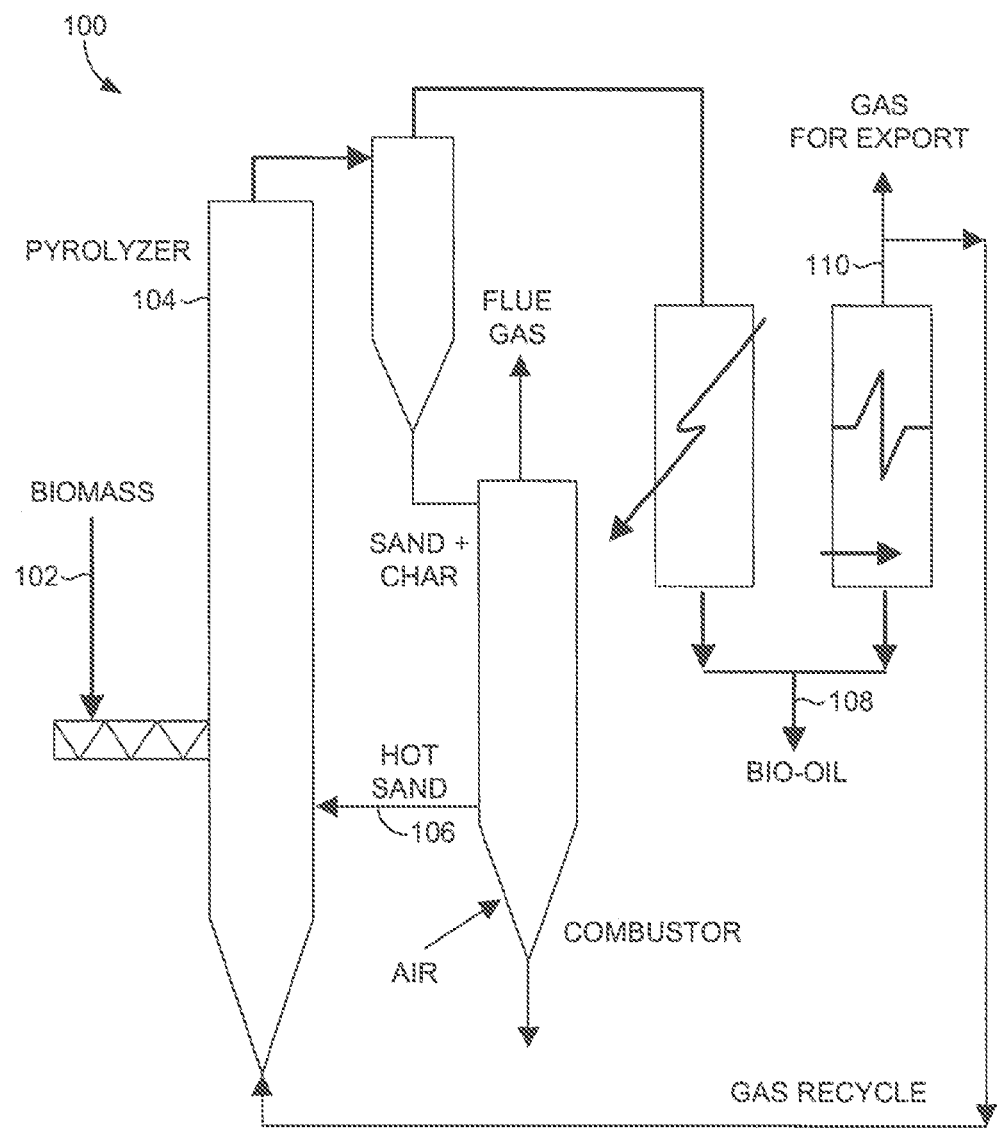

METHOD OF PRODUCING AN ALCOHOL-CONTAINING PYROLISIS PRODUCT

CROSS-REFERENCE TO RELATED APPLICATIONS

This application claims priority to U.S. Provisional Application Ser. No. 61/990,182 filed May 8, 2014, herein incorporated by reference in its entirety.

FIELD

The present invention relates to methods for producing pyrolysis products. In particular, the present invention relates to methods for producing alcohol-containing pyrolysis products.

BACKGROUND

In general, pyrolysis is a thermal degradation process in which large molecules are broken or cracked into smaller molecules in the presence of little if any oxygen. A wide variety of hydrocarbon materials can be pyrolyzed to produce vapor, liquid and solid materials into more readily useable forms. Pyrolysis is generally distinct from other processes that use both heat and additional chemical reactivity to alter molecular structure, such as processes that usually take place in reactive (non-inert) atmospheres, e.g., hydroprocessing/hydrotreatment in the presence of hydrogen-containing gas, sulfiding in the presence of a sulfur-containing gas, and the like.

Pyrolysis has been used to produce high viscosity tars from biomass materials for centuries. More recently, pyrolysis technology has been developed to increase yield and quality of vapor and liquid products.

U.S. Patent Application Publication No. 2009/0151253 discloses methods and systems to convert carbonaceous materials (such as biomass) into synthesis gas and other downstream products (such as alcohols). In certain embodiments, pyrolysis is performed in the presence of a catalyst such as heterogeneous catalysts (such as $SiO_2$—$Al_2O_3$, $Pt/SiO_2$—$Al_2O_3$, $WO_x/ZrO_2$, $SO_x/ZrO_2$), zeolites (such as HY-zeolite, alpha-zeolite, HZSM-5, ZSM-5, or klinoptilolite), acid catalysts, clay catalysts (e.g., acidified or activated clay catalysts), Al-MCM-41 type mesoporous catalysts, activated alumina, CoMo catalysts, and Ni/Al co-precipitated catalysts. In some embodiments, a cation such as $K^+$, $Li^+$, or $Ca^{2+}$ can be used to increase the selectivity and yield of char and/or to lower the selectivity and yield of tar during pyrolysis.

U.S. Pat. No. 8,202,332 discloses processes for fractional catalytic pyrolysis of biomass materials. The processes involve the use of a suitable catalyst in a fluidized bed pyrolysis system. Suitable catalysts are described as including H-ZSM-5, an aluminosilicate zeolite catalyst, and super acid catalysts, such as sulfated zirconia super acid catalysts.

U.S. Pat. No. 8,293,952 describes the production of pyrolysis products having a greater stability than pyrolysis products obtained from conventional pyrolysis production processes by using a basic metal oxide catalyst, such as a Group 2, Group 3, or Group 4 metal from the IUPAC Periodic Table of Elements.

SUMMARY

In various aspects, higher quality liquid products and/or higher quality condensable vapor products can be produced from a pyrolyzed feedstock. The pyrolysis products can be relatively easily recovered and are appreciably stable over a greater period of time, relative to current pyrolysis products.

One aspect of the invention relates to a method of producing an alcohol-containing pyrolysis product. The method comprises pyrolyzing a hydrocarbon feedstock in the presence of a catalyst system, the catalyst system comprising a basic metal oxide catalyst and a supported hydrogenation metal catalyst to produce a pyrolysis product that contains at least one alcohol, wherein the basic metal oxide catalyst is comprised of at least one metal from Group 2, Group 3 including Lanthanides and Actinides, or Group 4 of the Periodic Table of Elements, and wherein the supported hydrogenation metal catalyst is comprised of at least one metal from Group 6 or Groups 8-10 of the Periodic Table of Elements.

Another aspect of the invention relates to a method for treating a pyrolysis bio-oil. The method comprises passing a pyrolysis bio-oil into a reactor comprising a catalyst system, the catalyst system comprising a basic metal oxide catalyst and a supported hydrogenation metal catalyst, to produce a processed pyrolysis bio-oil having reduced quantities of ketones and aldehydes in comparison to the pyrolysis bio-oil.

BRIEF DESCRIPTION OF THE DRAWINGS

The FIGURE schematically illustrates an example of a configuration of a pyrolysis reactor suitable for producing pyrolysis bio-oil.

DETAILED DESCRIPTION

Introduction

In various aspects, use of catalysts according to the present invention provides pyrolysis products that have greater stability than pyrolysis products obtained from conventional pyrolysis production processes. The pyrolysis products provided by the processes of the present invention can generally be lower in aldehyde concentration and/or higher in alcohol than pyrolysis products provided from conventional processing. Having a pyrolysis product that has lower aldehyde content and/or a greater alcohol content can advantageously provide additional stability to the product, and can enable a wider variety of end uses and higher quality products.

In spite of the advances in pyrolysis oil production, problems can still exist with product quality, such as stability of the products produced, particularly in the case of pyrolysis liquid products produced from significant quantities of biomass materials. Over time, the viscosity of pyrolysis liquid products tends to increase as a result of polymerization reactions taking place. Heating the liquids (i.e., the condensed pyrolysis liquids) accelerates the polymerization reactions, in particular the reaction between formaldehyde and phenol, which are typically present in appreciable quantities. This instability can make transportation and long term storage of pyrolysis liquids a challenge.

U.S. Pat. No. 8,293,952 describes methods for partially stabilizing a pyrolysis bio-oil by, for example, including a basic metal oxide catalyst in the pyrolysis environment. This can allow for production of a pyrolysis oil product with a reduced content of aldehydes. The reduced content of aldehydes is due in part to the basic metal oxide catalyst facilitating reactions analogous to the Cannizzaro reaction in the pyrolysis environment. Although the basic metal oxide catalyst can reduce the quantity of some aldehydes within a pyrolysis oil, the basic metal oxide catalyst has a reduced or minimal ability to catalyze similar reactions for ketones or other oxygenated hydrocarbons. Additionally, some aldehydes such as hydroxyacetaldehyde may have a reduced likelihood of reacting in the presence of the base metal oxide catalyst. As a side-product of this reaction, hydrogen is also produced.

It has been unexpectedly discovered that the hydrogen produced by contacting a pyrolysis oil with a basic metal oxide catalyst can be used to produce a further improved and/or stabilized pyrolysis oil product. The hydrogen produced in-situ from the reactions with the base metal oxide catalyst can be used to convert oxygenated hydrocarbons with carbonyl functionality such as ketones, carboxylic acids and/or additional aldehydes into molecules with reduced carbonyl functionality such as alcohols or dialcohols if a catalyst including a hydrogenation metal is provided in the reaction environment. An example of a catalyst including a hydrogenation metal is a catalyst having a Group VIII metal (such as Pt, Pd, or Ni) on a support.

In various aspects described herein, a novel catalytic process for stabilization of bio-oil during its manufacture is provided. This process makes use of a combination of two different chemistries. In the first chemistry, the base-catalyzed disproportionation reaction of aldehydes to produce alcohols and acids is used to reduce aldehyde concentrations and generate hydrogen precursors. As an example involving formaldehyde molecules as a representative aldehyde, the net effect of this chemistry would be to convert two formaldehyde molecules and one water molecule into one molecule of methanol, one molecule of carbon dioxide, and one molecule of hydrogen. Significant reduction of the aldehyde concentration in the resultant bio-oil will result in a more stable product. In addition, the in-situ generation of methanol comes at no cost to the producer, and has a further stabilization effect on the bio-oil.

In the second chemistry, the hydrogen that has been generated in-situ via the first type of chemistry described above can then be used to further stabilize the bio-oil by converting carbonyl containing molecules such as ketones, carboxylic acids and/or additional aldehydes to alcohols. In some aspects, this can result in a reduced content of carbonyl containing molecules such as ketones and/or aldehydes relative to a pyrolysis oil product that is stabilized using only a basic metal oxide catalyst. Additionally or alternately, this can result in an increased content of alcohols, including poly-ols. Because the conversion of carbonyl containing molecules such as ketones and/or aldehydes is performed using in-situ hydrogen, no additional hydrogen is required to convert the carbonyl containing molecules such as ketones and/or aldehydes to alcohols. This in-situ hydrogen has a relatively low concentration relative to the total gas flow, and likely would be used (at best) as a fuel gas for the refinery. Instead, by including a supported hydrogenation metal that can make use of the in-situ hydrogen to further stabilize the pyrolysis oil, the resulting further stabilized pyrolysis oil can have a reduced hydrogen demand when subsequently processed in a deoxygenation reactor, hydrotreatment reactor, and/or other type of hydroprocessing for deoxygenating the further stabilized pyrolysis oil.

As will be described in greater detail herein, a catalyst system is utilized in a reactor to stabilize the bio-oil during manufacture. The catalyst system is comprised of a basic metal oxide catalyst in combination with a supported hydrogenation metal catalyst. In one embodiment, the basic metal oxide catalyst is separate and distinct from the supported hydrogenation metal catalyst, where the hydrogenation metal is impregnated or dispersed on a refractory support or carrier, such as alumina, silica, silica-alumina, titania, and/or zirconia. In an alternative embodiment, the hydrogenation metal is supported on the basic metal oxide catalyst. For example, the hydrogenation metal can be impregnated or otherwise dispersed on the basic metal oxide catalyst. The use of the catalyst system comprising at least one basic metal oxide catalyst in combination with at least one supported hydrogenation metal catalyst provides for a pyrolysis product, such as pyrolysis bio-oil or a processed pyrolysis bio-oil, that has reduced amounts of aldehydes and other carbonyl containing molecules such as ketones when compared to a product produced without the combination of the basic metal oxide catalyst and the hydrogenation metal catalyst. In some embodiments, the pyrolysis bio-oil may also have reduced amounts of unsaturated hydrocarbonaceous compounds when compared to a pyrolysis product that was manufactured without this combination of catalysts. In one embodiment, the catalyst system comprises at least one of a Group 2, Group 3, or Group 4 metal as the basic metal oxide catalyst and at least one of a Group VIII (groups 8-10 of the IUPAC periodic table) or Group VI metal as the hydrogenation metal catalyst.

The FIGURE schematically illustrates an example of a configuration 100 of a pyrolysis reactor suitable for producing pyrolysis bio-oil. As will be discussed in greater detail herein, bio-oil 108 can be produced from pyrolysis of biomass 102, such as wood chips or corn stover. Depending on the source, bio-oil 108 can be a complex mixture of organic oxygenates, characterized by high oxygen content (>35%), reactive oxygen functional groups, thermal instability, corrosivity, low energy content and a significant water fraction (10-20%), making it unsuitable for use as a refinery feedstock or transportation fuel without significant further upgrading. Bio-oil 108 can typically be produced using a fast pyrolysis process, where dry solid biomass is converted to liquid products using a reactor with high heat transfer rates, e.g., a fluidized bed reactor.

In a fast pyrolysis reactor, biomass 102 can be fed to a pyrolyzer 104 where it is contacted with a circulating heat transfer medium, typically a fine, hot sand 106, resulting in high heating rates, on the order of 1000° C./sec. Average temperatures at the outlet of the pyrolyzer are ~500° C., with a typical residence time of less than two seconds. The biomass 102 undergoes thermal depolymerization of the lignin and cellulose molecules, resulting in a complex mixture of oxygenated organics following rapid cooling. In addition to the bio-oil produced, a gas 110 (comprising predominately CO, $CO_2$, and $H_2O$) and char can be formed. The char typically circulates with the sand back to the combustor where it provides the heat required to bring the sand back to the desired temperature for the pyrolyzer 104.

An example of a bio-oil 108 produced via a fast pyrolysis reactor similar to the configuration shown in the FIGURE can be a complex mixture of oxygenated organics comprising predominately acids, aldehydes, ketones, phenolics, and alcohols. The composition varies with biomass source and processing. For example, the acids can be comprised predominately of formic (0.3-9.1 wt. %) and acetic acid (0.5-12 wt. %). The aldehydes can be comprised primarily of formaldehyde (0.1-3.3 wt. %) and acetaldehyde (0.1-8.5 wt. %). Other significant oxygenates can include phenol (0.1-3.8 wt. %) and furfural alcohol (0.1-5.2 wt. %). An example of such compositional data can be found in "Exploratory Studies of Fast Pyrolysis Oil Upgrading", F. H. Mahfud, Rijksuniversiteit Groningen, Nov. 16, 2007, ISBN 978-90-367-3226-9.

In this discussion, the terms "pyrolyze" and "pyrolyzing" are considered to be the act of converting a compound by pyrolysis. Pyrolysis is considered to be a chemical process in which a feed material is converted to one or more products by heat. By this definition, reactions that occur by heating in the presence of substantially reactive compounds (e.g., oxygen, hydrogen, sulfur-containing gases, and the like, but not including catalysts) to cause any significant degree of reaction involving (e.g., oxidation of) the feed material, such as by side reactions, are substantially excluded. The terms "thermolysis" or "thermal reaction" are considered to be synonyms for the term pyrolysis. According to the present invention, the term "torrefaction" is also considered as being within the definition of pyrolysis.

Feedstock

A wide range of feedstocks of various types, sizes, and moisture contents can be processed according to aspects of the present invention. Feedstocks that can be used in aspects of the present invention can comprise any hydrocarbon that can be thermally decomposed and/or transformed. Preferably, the feedstock comprises biomass, particularly biomass not typically processed or easily processable through chemical reactions. For example, the feedstocks can be comprised of at least 10 wt %, or at least 30 wt %, or at least 50 wt %, or at least 70 wt %, or at least 90 wt % biomass, based on total weight of feedstock that is processed or supplied to the thermal or pyrolysis reactor.

The term "biomass," for the purposes of the present invention, is considered any material not derived from fossil/mineral resources and comprising carbon, hydrogen, and oxygen. Examples of biomass can include, but are not limited to, plant and plant-derived material, algae and algae-derived material, vegetation, agricultural waste, forestry waste, wood waste, paper waste, animal-derived waste, poultry-derived waste, municipal solid waste, cellulose and cellulosics, carbohydrates or derivates thereof, charcoal, and the like, and combinations thereof. The feedstock can also comprise pyrolyzable components other than biomass, such as fossil/mineral fuels (e.g., coal, crude or refined petroleum feedstocks, and the like, as well as combinations thereof).

Additional or alternate examples of biomass that can be included as feedstock components include, but are not limited to, timber harvesting residues, softwood chips, hardwood chips, tree branches, tree stumps, leaves, bark, sawdust, off-spec paper pulp, corn, corn cob, corn stover, wheat straw, rice straw, sugarcane, bagasse, switchgrass, miscanthus, animal manure, municipal garbage, municipal sewage, commercial waste, grape pumice, almond shells, pecan shells, coconut shells, coffee grounds, grass pellets, hay pellets, wood pellets, cardboard, paper, plastic, cloth, and combinations thereof.

The biomass to be pyrolyzed may be ground prior to pyrolyzing. For example, the biomass can be ground in a mill until a desired particle size is achieved. In one embodiment, the particle size of the biomass to be pyrolyzed can be sufficient (with or without grinding) to pass through a 30 mm screen, for example a 20 mm screen, a 10 mm screen, a 5 mm screen, or a 1 mm screen.

Catalyst

The catalyst of the present invention comprises, consists essentially of, or is a combination of a basic metal oxide catalyst and a hydrogenation metal catalyst. Both of the basic metal oxide catalysts and the hydrogenation metal catalysts will be discussed separately below. In some aspects, the hydrogenation metal catalyst can be supported on the basic metal oxide catalyst. In other aspects, the hydrogenation metal catalyst can be supported on a refractory oxide support or carrier and is separate from the basic metal oxide catalyst.

As mentioned, in various embodiments, a basic metal oxide catalyst can be used in combination with a hydrogenation metal catalyst. When used together in a single catalyst, the catalyst becomes bifunctional, as it comprises metals active for hydrogenation supported on solid base catalysts, such as in the form of a mixed metal oxide.

A hydrogenation metal catalyst, as used herein, is a catalyst known to be used for hydrogenation reactions, and could be, for example, a metal from Group VI (group 6 of the IUPAC periodic table) or Group VIII (groups 8-10 of the IUPAC periodic table). For instance, a hydrogenation metal catalyst that may be used in embodiments described herein may comprise at least one Group VIII metal, such as platinum (Pt), iron (Fe), cobalt (Co), and/or nickel (Ni). In addition to or instead of a Group VIII metal, the hydrogenation metal catalyst may comprise at least one Group VI metal, preferably molybdenum (Mo) and/or tungsten (W). Thus, in various aspects, the hydrogenation metal can be Pt, Fe, Co, Ni, Pd, Mo, W, or a combination thereof.

The hydrogenation metal can be supported on a catalyst support. In aspects where the hydrogenation catalyst is separate from the basic metal oxide catalyst, any convenient type of refractory metal oxide support can be used. Examples of suitable support materials include silica, alumina, silica-alumina, zirconia, titania, or combinations thereof. The amount of hydrogenation metal supported on a catalyst can be from about 0.05 wt % to about 10 wt % of the weight of the catalyst. For example the amount of hydrogenation metal can be at least about 0.05 wt % of the weight of the catalyst, or at least about 0.08 wt %, or at least about 0.1 wt %, or at least about 0.15 wt %, or at least about 0.2 wt %, or at least about 0.25 wt %, or at least about 0.3 wt %, or at least about 0.4 wt %, or at least about 0.5 wt %. Additionally or alternately, the amount of hydrogenation metal can be about 10 wt % or less, such as about 5 wt % or less, or about 3 wt % or less, or about 2.5 wt % or less, or about 2.0 wt % or less, or about 1.5 wt % or less. Each of the above upper and lower bounds is explicitly contemplated in combination with each other. Thus, ranges that are explicitly contemplated include about 0.05 wt % to about 5 wt %, or about 0.05 wt % to about 2.5 wt %, or about 0.05 wt % to about 1.5 wt %, or about 0.08 wt % to about 2.5 wt %, or about 0.08 wt % to about 2.0 wt %, or about 0.08 wt % to about 1.5 wt %, or about 0.1 wt % to about 2.5 wt %, or about 0.1 wt % to about 2.0 wt %, or about 0.1 wt % to about 1.5 wt %, or about 0.1 wt % to about 5 wt %.

In other aspects, the hydrogenation metal catalyst can be placed or supported on the basic metal oxide catalyst, such as by impregnation. For example, a hydrogenation metal of Pt may be used in combination with La/$ZrO_2$. Here, the Pt may be added to La/$ZrO_2$ via impregnation. This effectively creates a bifunctional catalyst. In still other aspects, a portion of the hydrogenation metal can be supported on the basic metal oxide catalyst while a second portion of the hydrogenation metal can be supported on a separate refractory oxide support.

The basic metal oxide catalyst, according to embodiments of present invention, is an active metal oxide catalyst that includes at least one oxide of at least one metal that provides a metal oxide catalyst having a measurable uptake of carbon dioxide upon heating. The basic metal oxide catalyst of embodiments described herein, when combined with a hydrogenous metal catalyst, is particularly advantageous, in that it can be used in the production of a pyrolysis product that is higher in quality and more highly stable than typical pyrolysis products.

In one embodiment of the invention, the basic metal oxide catalyst has an uptake of carbon dioxide at 100° C. of at least 0.03 mg/m$^2$ of the metal oxide catalyst, for example at least 0.04 mg/m$^2$, at least 0.05 mg/m$^2$, at least 0.06 mg/m$^2$, or at least 0.08 mg/m$^2$. Although the upper limit on the carbon dioxide uptake is not critical, in general the metal oxide catalysts useful herein will have a carbon dioxide uptake at 100° C. of not greater than 10 mg/m$^2$ of the metal oxide catalyst, for example not greater than 5 mg/m$^2$, not greater than 3 mg/m$^2$, not greater than 2 mg/m$^2$, of not greater than 1 mg/m$^2$. Typically, the metal oxide catalysts useful herein have a carbon dioxide uptake from 0.05 mg/m$^2$ to 1 mg/m$^2$ of the metal oxide catalyst. The metal oxide catalysts can have a particular benefit in ultimately providing relatively high quality liquid pyrolysis products or pyrolysis oils, particularly liquid products having a substantial quantity of alcohol components (e.g., at a level relatively higher than conventional pyrolysis products/oils).

In order to determine the carbon dioxide uptake of a metal oxide catalyst according to embodiments of the present invention, the following procedure is to be followed. A sample of the metal oxide catalyst is dehydrated by heating the sample to about 200° C. to about 500° C. in flowing air until a constant weight, the "dry weight," is obtained. The temperature of the sample is then reduced to about 100° C., and carbon dioxide is passed over the sample, either continuously or in pulses, again until constant weight is obtained. The increase in weight of the sample in terms of mg/mg of the sample based on the dry weight of the sample is the amount of adsorbed carbon dioxide.

The carbon dioxide adsorption can be measured using a Mettler TGA/SDTA 851 thermogravimetric analysis system under ambient pressure. The metal oxide catalyst sample can be dehydrated in flowing air to about 500° C. for about one hour. The temperature of the sample can then be reduced in flowing inert gas (e.g., helium) to the desired adsorption temperature, e.g., in this case about 100° C. After the sample has equilibrated at the desired adsorption temperature in the inert gas, the sample can be subjected to about 20 separate pulses (e.g., about 12 seconds per pulse) of a gaseous mixture comprising $CO_2$ (e.g., the gaseous mixture can comprise about 10 wt % carbon dioxide with the remainder being an inert gas such as helium). After each pulse of the adsorbing gas, the metal oxide catalyst sample can be flushed with flowing inert gas (e.g., helium) for about 3 minutes. The increase in weight of the sample in terms of mg/mg adsorbent based on the adsorbent weight after treatment at about 500° C. represents the amount of adsorbed carbon dioxide. The surface area of the sample can be measured in accordance with the method of Brunauer, Emmett, and Teller (BET), published as ASTM D 3663, to provide the carbon dioxide uptake in terms of mg carbon dioxide/m$^2$ of the metal oxide catalyst. Specific examples of how to determine carbon dioxide adsorption, including a further description of certain preferred catalysts useful according to aspects of the present invention, are further described, e.g., in U.S. Pat. Nos. 6,844,291 and 6,995,111, the contents of each of which are incorporated herein by reference.

The basic metal oxide catalyst can be comprised of oxides of at least one metal from Group 2, Group 3 (including Lanthanides and Actinides), and Group 4 of the Periodic Table of Elements (New IUPAC Notation). In one embodiment, the basic metal oxide catalyst includes at least one Group 2 metal. In another embodiment, the basic metal oxide catalyst includes at least one Group 3 metal. In another embodiment, the basic metal oxide catalyst includes at least one Group 4 metal. In another embodiment, the basic metal oxide catalyst includes at least one Lanthanide, in another embodiment, the basic metal oxide catalyst includes at least one Actinide.

The basic metal oxide catalyst can also be comprised of more than one oxide of different metal components. Examples of more than one oxide of different metal components can include, but are not limited to, oxides of at least one Group 2 metal and at least one Group 3 metal (including Lanthanides and Actinides); oxides of at least one Group 3 metal (including Lanthanides and Actinides), and at least one Group 4 metal; and oxides of at least one Group 2 metal and at least one Group 4 metal.

A basic metal oxide catalyst according to aspects of the present invention can preferably be comprised of, or can consist essentially of (with a non-catalytic binder, such as silica and/or alumina or the like, being the remainder of the composition), about 1 wt % to 100 wt %, based on total weight of the catalyst, of an oxide of at least one metal that provides a metal oxide catalyst having a measurable uptake of carbon dioxide upon heating. In a particular embodiment, the basic metal oxide catalyst according to aspects of the present invention can be comprised of or can consist essentially of 1 wt % to 90 wt %, for example 1 wt % to 70 wt %, 1 wt % to 50 wt %, or 1 wt % to 30 wt % of an oxide of the at least one metal, based on total weight of the catalyst, such that the catalyst has a measurable uptake of carbon dioxide upon heating. In this embodiment, the remainder of the composition can be comprised of a binder that is non-catalytic for the pyrolysis process, which can include, but is not necessarily limited to, silica, alumina, silica-alumina, or the like, or a combination thereof.

The basic metal oxide catalyst is preferably in particle form and can preferably have an average particle diameter from 0.01 μm to 500 μm, for example from 0.05 μm to 300 μm or from 0.1 μm to 100 μm.

In one embodiment, the basic metal oxide catalyst can have a BET surface area of greater than 10 m$^2$/g, such as from above 10 m$^2$/g to about 300 m$^2$/g. Additionally or alternately, the basic metal oxide catalyst can have a BET surface area greater than 20 m$^2$/g, such as from above 20 m$^2$/g to 250 m$^2$/g. Further additionally or alternately, the basic metal oxide catalyst can have a BET surface area greater than 25 m$^2$/g, such as from above 25 m$^2$/g to 200 m$^2$/g.

Group 2 metals that can be included as an oxide component in the catalyst of aspects of the present invention are beryllium, magnesium, calcium, strontium, barium, radium, and combinations thereof. Examples of preferred oxides containing at least one Group 2 metal include, but are not limited to, one or more of magnesium oxides, calcium oxides, and hydrotalcite ($Mg_6Al_2(CO_3)(OH)_{16} \cdot 4H_2O$), which can, in one embodiment, be calcined to form a basic magnesium aluminum oxide catalyst, representing a Group 2 metal oxide catalyst of aspects of the present invention.

Group 3 metals (including Lanthanides and Actinides) that are naturally occurring and can be included as an oxide component in the catalyst of aspects of the present invention are scandium, yttrium, lanthanum, actinium, cerium, praseodymium, neodymium, samarium, europium, gadolinium, terbium, dysprosium, holmium, erbium, thulium, ytterbium, lutetium, thorium, protactinium, and uranium. Examples of preferred Group 3 metals include, but are not limited to, yttrium, cerium, praseodymium, and combinations thereof.

Group 4 metals that can be included as an oxide component in the catalyst of aspects of the present invention are titanium, zirconium, and hafnium. One example of a preferred Group 4 metal includes zirconium.

The basic metal oxide catalyst can be prepared using a variety of methods. The basic metal oxide catalyst can be made from active metal oxide precursors, such as metal salts or preferably Group 2, Group 3, and/or Group 4 metal salts/precursors. Other suitable sources of the metal oxide(s) can include compounds that form these metal oxides during calcination, e.g., oxychlorides, nitrates, and the like. A further suitable source of the basic metal oxides can include salts containing a cation of the Group 2, Group 3 or Group 4 metal(s), e.g., metal halides, oxyhalides, nitrates, sulfates, alkoxides, acetates, and the like. See, e.g., U.S. Pat. Nos. 6,844,291; 6,995,111; 7,199,278; and 7,411,106, the contents of which are hereby incorporated by reference.

In one embodiment, the basic or active metal oxide can be hydrothermally treated under conditions that include a temperature of at least 80° C., preferably at least 100° C. The hydrothermal treatment may take place in a sealed vessel at greater than atmospheric pressure. However, a preferred mode of treatment involves the use of an open vessel under reflux conditions. Without being bound by theory, it is believed that agitation of the metal oxide in a liquid medium, for example, by the action of refluxing liquid and/or stirring, can promote effective interaction of the oxide with the liquid medium. The duration of the contact of the oxide with the liquid medium (i.e., in batch processes) can preferably be at least 1 hour, for example at least 8 hours. The liquid medium for this treatment can have a pH of about 6 or greater, preferably about 7 or greater, e.g., about 8 or greater. Non-limiting examples of suitable liquid media include water, hydroxide solutions (including hydroxides of $NH_4^+$, $Na^+$, $K^+$, $Mg^{2+}$, $Ca^{2+}$, and the like, and combinations thereof), carbonate and/or bicarbonate solutions (including carbonates and/or bicarbonates of $NH_4^+$, $Na^+$, $K^+$, $Mg^{2+}$, $Ca^{2+}$, and the like, and combinations thereof), pyridine and its derivatives, alkyl/hydroxylamines, and the like, and combinations thereof.

In another embodiment, the basic or active metal oxide can be prepared by subjecting a liquid solution, such as an aqueous solution, comprising a source of ions of the metal, such as a metal salt, to conditions sufficient to cause precipitation of a hydrated precursor to the solid oxide material, such as by the addition of a precipitating reagent to the solution. Conveniently, the precipitation can be conducted at a pH above 7. For example, the precipitating agent can be a base such as sodium hydroxide or ammonium hydroxide.

The temperature at which the liquid medium is maintained during the precipitation can generally be less than about 200° C., for example in the range from about 0° C. to about 200° C. or from about 20° C. to about 100° C. The resulting gel can then be hydrothermally treated at temperatures of at least 80° C., preferably at least 100° C. The hydrothermal treatment can typically take place in a vessel at atmospheric pressure. The gel, in one embodiment, can be hydrothermally treated for up to 10 days, for example up to 5 days or up to 3 days.

The hydrated precursor to the basic or active metal oxide can then be recovered, for example by filtration or centrifugation, and washed and dried. The resulting material can preferably be calcined, for instance in an oxidizing atmosphere at a temperature of at least 400° C., for example of at least 500° C., from about 600° C. to about 900° C., or from about 650° C. to about 800° C., to form a solid oxide material. The calcination time can typically be up to 48 hours, for example from about 0.5 hours to about 24 hours or from about hour to about 10 hours. In a particular embodiment, batch-wise calcination can be carried out at a temperature of about 700° C. for about 1 hour to about 3 hours.

In one method, the basic or active metal oxide can be prepared by the thermal decomposition of metal-containing compounds at relatively high temperatures. Non-limiting examples of such metal-containing compounds can include magnesium and/or barium oxalates, which can be thermally decomposed at temperatures of up to 600° C. in flowing air. Thus, prepared metal oxides can usually have relatively lower BET surface area, e.g., less than 30 $m^2/g$.

In another method, the basic or active metal oxide can be prepared by hydrolysis of metal-containing compounds followed by dehydration and calcination. As a non-limiting or preferred example, MgO can be hydroxylated by mixing with deionized water, thus forming a white slurry. The slurry can slowly be heated to dryness on a heating plate to form a white powder. The white powder can further be dried in a vacuum oven at about 100° C. for at least 4 hours, for example up to 12 hours. The dried white powder can then be calcined (e.g., in air) at a temperature of at least 400° C., for example up to 550° C. or up to 500° C. Thus-prepared active metal oxides can generally exhibit higher BET surface area (e.g., from about 30 $m^2/g$ to about 300 $m^2/g$) than those prepared by thermal decomposition of the active metal oxide precursors.

In yet another method, the basic or active metal oxide can be prepared by the so-called aerogel method (see Koper, O. B., Lagadic, I., Volodin, A. and Klabunde, K., J. Chem. Mater., 1997, 9, 2468-2480). As one example of this method, Mg powder can be reacted under inert (nitrogen) purge with anhydrous methanol to form $Mg(OCH_3)_2$ solution in methanol. The resultant $Mg(OCH_3)_2$ solution can be added to toluene. Water can then be added dropwise to the $Mg(OH)_2$ solution in methanol-toluene, e.g., under vigorous stirring. The resultant colloidal suspension of $Mg(OH)_2$ can be placed in an autoclave, e.g., pressurized to about 100 psig (about 690 kPag) with dry nitrogen, and can be heated slowly to a final pressure of about 1000 psig (about 6.9 MPag). The (supercritical) solvent can be vented to produce a fine white powder of substantially $Mg(OH)_2$. Nanocrystalline MgO can be obtained by heating the fine white powder at about 400° C. under vacuum. Active metal oxides prepared by this method can tend to have the highest BET surface area, generally at least about 300 $m^2/g$.

In one embodiment, where the basic or active metal oxide(s) used herein can comprise, or can consist essentially of, two or more oxides selected from Groups 2, 3, and 4 (i.e., a mixed metal oxide, or MMO), the mixed metal oxide may be prepared by impregnation of a precursor to a second oxide onto a preformed oxide. In an alternate embodiment, the first formed oxide may be hydrothermally treated prior to impregnation. For example, a Group 3/Group 4 mixed metal oxide can be prepared by impregnating a hydrothermally treated hydrated oxide of the Group 4 metal with an aqueous solution containing an ion of the Group 3 metal, followed by drying. The resulting material can then be calcined, preferably in an oxidizing atmosphere, e.g., at a temperature of at least about 400° C., for example at least about 500° C., from about 600° C. to about 900° C., or from about 650° C. to about 800° C. The calcination time may be up to 48 hours, for example from about 0.5 hours to about 24 hours or from about 1 hour to about 10 hours. In a particular embodiment, batch-wise calcination can be carried out at a temperature of about 700° C. for about 1 hour to about 3 hours.

In yet another embodiment, where the basic or active metal oxide(s) used herein can comprise, or can consist essentially of, a mixed metal oxide, it may be prepared by combining a first liquid solution comprising a source of at least one of the Group 2, 3, or 4 metals with a second liquid solution comprising a source of an ion of at least one other Group 2, 3, or 4 metal. This combination of two solutions can take place under conditions sufficient to cause co-precipitation of a hydrated precursor to the mixed oxide material as a solid from the liquid medium. Alternately, the sources of the all the anions of the Group 2, 3, and/or 4 metal oxides may be combined in a single solution. This solution may then be subjected to conditions sufficient to cause co-precipitation of the hydrated precursor to the solid mixed oxide material, such as by the addition of a precipitating reagent to the solution. For example, the precipitating agent(s) can preferably comprise (or be) a base, such as sodium or ammonium hydroxide. Water is typically a preferred solvent for these solutions.

The temperature at which the liquid medium(s) is maintained during the precipitation or co-precipitation can typically be less than about 200° C., for example from about 0° C. to about 200° C. A particular range of temperatures for co-precipitation can be from about 20° C. to about 100° C. The resulting gel can preferably then be hydrothermally treated at a temperature of at least about 80° C., for example at least about 100° C. The hydrothermal treatment can typically take place in a sealed vessel, e.g., at greater than atmospheric pressure. The gel, in one embodiment, can be hydrothermally treated for up to about 10 days, for example up to about 5 days or up to about 3 days.

The hydrated precursor to the basic metal oxide(s) can then be recovered, for example by filtration or centrifugation, and washed and dried. The resulting material can preferably be calcined, for instance in an oxidizing atmosphere at a temperature of at least 400° C., for example of at least 500° C., from about 600° C. to about 900° C., or from about 650° C. to about 800° C., to form a solid oxide material. The calcination time can typically be up to 48 hours, for example from about 0.5 hours to about 24 hours or from about 1 hour to about 10 hours. In a particular embodiment, batch-wise calcination can be carried out at a temperature of about 700° C. for about 1 hour to about 3 hours.

In one embodiment of the invention, the basic metal oxide catalyst can be comprised of hydrotalcite or a calcined hydrotalcite. The hydrotalcite can be a naturally occurring hydrotalcite or a synthetically produced hydrotalcite, such as described in U.S. Pat. No. 6,951,830.

Naturally occurring hydrotalcite is a mineral found in relatively small quantities in a limited number of geographical areas, principally in Norway and in the Ural Mountains. Natural hydrotalcite has a variable composition depending on the location of the source. Natural hydrotalcite is a hydrated magnesium-, aluminum-, and carbonate-containing composition, which has been found to have a representative composition of $(Mg_6Al_2(CO_3)(OH)_{16}.4H_2O)$. Natural hydrotalcite deposits are generally found intermeshed with spinel and other minerals, such as penninite and/or muscovite, from which it is difficult to separate the natural hydrotalcite.

Synthetically produced hydrotalcite can be made to have the same composition as natural hydrotalcite, or, due to flexibility in the synthesis, it can be made to have a different composition by replacing the carbonate anion with other anions, e.g., a phosphate ion. In addition, the Mg/Al ratio can be varied to control the basic properties of the hydrotalcite. A phosphate-modified synthetic hydrotalcite can also be used. Methods of making such compositions are described in U.S. Pat. No. 4,883,533. Other types of hydrotalcites can also be used, such as those described in U.S. Pat. Nos. 3,539,306; 4,656,156; and 4,904,457.

Hydrotalcite compositions containing pillaring organic, inorganic, and mixed organic/inorganic anions can also be used. Such materials are described in greater hydrotalcite clays having large inorganic and/or organic anions located interstitially between positively charged layers of metal hydroxides of the general formula $[Mg_{2x}Al_2(OH)_{4x+4}]Y_{2/n}{}^n.ZH_2O$, where Y can be a relatively large organic anion, e.g., selected from the group consisting of lauryl sulfate, p-toluenesulfonate, terephthalate, 2,5-dihydroxy-1,4-benzenedisulfonate, and 1,5-naphthalenedisulfonate, or where Y can be an anionic polyoxometalate of vanadium, tungsten, or molybdenum. In the above cases, x can be from 1.5 to 2.5, n can be 1 or 2, and Z can be from 0 to 3, except that, when Y is the polyoxometalate, n can be 6.

An aggregated synthetic hydrotalcite can also be used. Preferably, the aggregated synthetic hydrotalcite can have a substantially spheroidal shape and an average spherical diameter of up to about 60 µm. Such a composition is described in greater detail in U.S. Pat. No. 5,364,828. This form of hydrotalcite can preferably be prepared from aqueous solutions of soluble magnesium and aluminum salts, which can be mixed in a molar ratio from about 2.5:1 to about 4:1, together with a basic solution containing at least a two-fold excess of carbonate and a sufficient amount of a base to maintain a pH of the reaction mixture in the range from about 8.5 to about 9.5.

Some synthetic hydrotalcites are commercially available, for example from Sasol North America, Inc., such as under the tradename Condea Pural MG70. Prior to use according to the process of aspects of the present invention, it may be desirable to calcine the hydrotalcite to remove at least a portion of the water inherently contained in the material. Suitable calcination conditions can include, but are not limited to, a temperature from about 300° C. to about 800° C., for example from about 400° C. to about 600° C., for a calcination time from about 1 hour to about 16 hours, for example from about 3 hours to about 8 hours.

According to embodiments of the present invention, the production of pyrolysis products can be achieved in the presence of the basic metal oxide catalyst in combination with the hydrogenation metal catalyst, as described herein. The basic metal oxide catalyst and the hydrogenation metal catalyst can optionally act to absorb heat, as well as carry out catalytic activity. Additional heat absorbing material can be used, if desired, along with the basic metal oxide catalyst in the pyrolysis process. For example, solid heat absorbing material can be added to a pyrolysis reactor along with the basic metal oxide catalyst. The solid heat absorbing material can be any solid capable of absorbing heat and does not adversely affect the ability of the basic metal oxide and the hydrogenation metal to catalyze conversion, e.g., of aldehydes and ketones to alcohols. Examples of solid heat absorbing material that can be used along with the basic metal oxide can include, but are not limited to, inert clays, glass materials, sand, char, and the like, and combinations thereof.

In one embodiment of the invention, solid heat absorbing material used in the pyrolysis reactor to carry out the pyrolysis process can be solely (about 100 wt % of) the basic metal oxide catalyst. In yet another embodiment, solid heat absorbing material used in the pyrolysis reactor to carry out the pyrolysis process can be a combination of the basic metal oxide catalyst and the hydrogenation metal catalyst. In still another embodiment, pyrolysis product can be produced by pyrolyzing feedstock in the presence of solid heat absorbing material containing from 1 wt % to below 100 wt % basic metal oxide and/or from 1 wt % to below 100 wt % supported hydrogenation metal catalyst, based on total weight of solid heat absorbing material provided to the pyrolysis reactor in which the pyrolysis process is carried out. In this embodiment, pyrolysis product can be produced by pyrolyzing feedstock in the presence of solid heat absorbing material containing from 1 wt to 99 wt %, for example from 1 wt % to 90 wt %, from 1 wt % to 70 wt %, from 1 wt % to 50 wt %, from 1 wt % to 30 wt %, or from 1 wt % to 20 wt %, of basic metal oxide and/or supported hydrogenation metal catalyst, based on total weight of solid heat absorbing material provided to the pyrolysis reactor in which the pyrolysis process is carried out.

In a particular embodiment of the invention, the total amount of solid heat absorbing material used in the pyrolysis reactor to carry out the pyrolysis process may contain not greater than 99 wt % of solid heat absorbing material other than the basic metal oxide catalyst or the supported hydrogenation metal catalyst, with the remainder being the basic metal oxide catalyst and/or the supported hydrogenation metal catalyst. In another embodiment, the total amount of solid heat absorbing material used in the pyrolysis reactor to carry out the pyrolysis process can contain not greater than 95 wt %, for example not greater than 90 wt %, not greater than 80 wt %, not greater than 70 wt %, not greater than 60 wt %, or not greater than 50 wt %, of solid heat absorbing material other than the basic metal oxide catalyst or the supported hydrogenation metal catalyst, with the remainder being the basic metal oxide catalyst and/or the supported hydrogenation metal catalyst.

Process Conditions

Pyrolysis can preferably be carried out in the presence of little to no oxygen. If oxygen is present, it can be present in an amount less that the stoichiometric amount required for complete combustion. Preferably, pyrolysis can be carried out in an environment (e.g., in the pyrolysis reactor) having an oxygen content of less than 40%, for example less than 30%, less than 20%, less than 10%, less than 5%, less than 1%, less than 0.5%, or less than 0.01% of the stoichiometric amount of oxygen required for complete combustion of the feedstock. In another preferred embodiment, pyrolysis can be carried out in the absence of any added oxygen (in which case oxygen may be present in trace amounts, but no oxygen is deliberately added).

Preferred pyrolysis conditions are typically those that minimize non-condensable gas formation and solid or char formation. Preferred conditions are also typically those that lead to condensable gas and liquid formation.

In one embodiment, pyrolyzed product can exit the pyrolysis reactor in the vapor phase. Preferably, the vapor phase can be passed through a filter to separate any solids from the more desirable product. The filtered vapors can then be condensed to form one or more liquid products.

Condensation can be carried out using any equipment suitable for such purpose. For example, condensation can be carried out using a condensation train to collect the desired products. The condensation train can comprise at least one chilled water condenser, at least one electrostatic precipitator, or at least one coalescence filter, as well as combinations thereof.

The pyrolysis temperature can be sufficiently high to convert a sufficient quantity of feed to desired product, but not so high to produce undesired quantities of non-condensable gas or undesired solid. Preferably, feed can be pyrolyzed at a temperature from 200° C. to 600° C., for example from 300° C. to 600° C. or from 400° C. to 500° C.

The pyrolysis pressure can be within a range that minimizes formation of non-condensable gas and solid product. The pressure can range from about 0 psig (about 0 kPag) to about 1000 psig (about 6.9 MPag), preferably from about 5 psig (about 35 kPag) to about 500 psig (about 3.5 MPag) or from about 10 psig (about 69 kPag) to about 200 psig (about 1.4 MPag).

Pyrolysis can generally be carried out for a time that enables a substantial quantity of feed to be converted into condensable vapor and/or liquid products. This can range over a wide period of time, depending upon pressure, temperature, and type of reactor used, inter alia. For example, pyrolysis can be carried out for a time from 0.1 second to 48 hours, for example from 0.1 second to 24 hours or from 0.1 second to 1 hour. Shorter times are generally more preferred, such as from 0.1 second to 1 minute or from 0.1 second to 10 seconds. Thus, in some embodiments, fast pyrolysis can be used. Fast pyrolysis is a high-temperature process in which feedstock is rapidly heated. In some embodiments, the feedstock can be heated in the absence of oxygen. The feedstock can advantageously decompose to generate predominantly vapor and solid (char) products/by-products. The vapor product can preferably be cooled and condensed to form one or more liquid products. Multiple steps of heating and cooling can be carried out to produce intermediate pyrolysis liquid products. Fast pyrolysis processes can typically produce from about 60 wt % to about 75 wt % condensable gas and liquid products, from about 15 wt % to about 25 wt % solid char, and from about 10 wt % to about 20 wt % non-condensable gas products, but these relative numbers can depend heavily on the particular feedstock composition.

Slow pyrolysis can also be used. In slow pyrolysis, the feedstock can preferably be heated to not greater than about 600° C. for a time period ranging from 1 minute to 24 hours, preferably from 1 minute to 1 hour. Vapor product typically does not escape as rapidly in slow pyrolysis as in fast pyrolysis. Thus, vapor products may react with each other as solid char and liquid are being formed. Rates of heating in slow pyrolysis can typically be slower than in fast pyrolysis. A feedstock can be held at constant temperature or slowly heated. Vapors can be continuously removed as they are formed.

Vacuum pyrolysis can additionally or alternately be used. In vacuum pyrolysis, the feedstock is maintained at less than atmospheric pressure (i.e., below 0 psig or 0 kPag, but above 0 psia or 0 kPaa). Vacuum conditions can be used to decrease the boiling point, to avoid adverse chemical reactions, and to reduce the heating duty by using relatively lower temperatures.

Pyrolysis product can contain water. As an example, condensed pyrolysis product can contain from 10 wt % to 30 wt % water. If desired, the water can be removed using any appropriate means, such as by flashing, decanting, distillation, membrane separation, or the like, or any combination thereof.

Reactor Type

Any reactor suitable for pyrolyzing feedstock can be used in the process of aspects of the present invention. Examples of reactors can include, but are not limited to, auger reactors, ablative reactors, rotating cones, fluidized-bed reactors (e.g., circulating fluidized-bed reactors), entrained-flow reactors, vacuum moving-bed reactors, transport-bed reactors, fixed-bed reactors, microwave-assisted pyrolysis reactors, and the like, and combinations thereof in series and/or in parallel.

In auger type reactors, feedstock and heat absorbing material (i.e., basic metal oxide and/or hydrogenation metals, including any other solid heat absorbing material that may be used) can be fed at one end of a screw. The screw can mix the heat absorbing material and feedstock for conveying them through the reactor.

In an ablative process, feedstock can be contacted against a heated metal surface. In general, the metal surface can spin at a relatively high speed within a bed of feedstock, which can prevent dilution of the products. As an alternative, the feedstock particles may be suspended in a carrier gas and introduced at a relatively high speed, e.g., through a cyclone. In one such embodiment, the walls of the cyclone can be heated. Also in such embodiment, the products are typically diluted with the carrier gas.

In a rotating cone reactor, feed and solid heat absorbing material (e.g., basic metal oxide catalyst and/or hydrogenation metal catalyst, optionally including sand) can be introduced into a rotating cone. As the cone is rotated, the solid heat absorbing material can be transported across the cone surface by centrifugal force. Like other shallow transport bed reactors, relatively fine particles can be used to obtain greater liquid yield.

In fluidized bed reactors, feedstock can be introduced into a bed of solid heat absorbing material (e.g., basic metal oxide catalyst and/or hydrogenation metal catalyst, optionally including sand) by a gas, which can usually comprise a recirculated product gas. High heat transfer rates from the fluidized, solid heat absorbing material can result in relatively rapid heating of the feedstock.

In circulating fluidized bed reactors, feedstock can be introduced into the reactor to contact a circulating fluidized bed of solid heat absorbing material (e.g., basic metal oxide catalyst and/or hydrogenation metal catalyst, optionally including sand). Gas, solid heat absorbing material, and feedstock typically all move together. Examples of transport gases can include, but are not limited to, recirculated product gases, combustion gases, relatively inert gases, and the like, and combinations thereof. High heat-transfer rates from the solid heat absorbing material can ensure relatively rapid heating of the feedstock. A separator system can separate product vapor from the solid heat absorbing material and any remaining char particles. The solid heat absorbing particles can preferably be reheated in a fluidized burner vessel and recycled to the reactor.

Product and Use

As pyrolysis products leave the reactor, they can be in the form of vapor, liquid, and/or solid. A substantial portion of the vapor can preferably be a condensable vapor, e.g., a condensable $C_3^+$ hydrocarbon. In a preferred embodiment, a substantial portion of the vapor exiting the reactor can be condensed to form a fuel or pyrolysis oil. These various products can be isolated by way of a condenser system. The products can be used as fuels and/or as a variety of chemicals.

In some aspects, the pyrolysis product of aspects of the present invention can be higher in alcohol content than the product produced from the same feedstock pyrolyzed in the absence of a basic metal oxide and/or in the absence of a basic metal oxide in combination with a hydrogenation metal catalyst. Additionally or alternately, the pyrolysis product can have an increased content of polyols and/or a reduced content of carbonyl containing molecules such as ketones and/or aldehydes. The total alcohol content can be heavily dependent on the feedstock used and the pyrolyzing conditions employed. In one embodiment, the pyrolysis product can be comprised of at least 1 wt % more alcohol, preferably at least 2 wt % more alcohol, for example at least 4 wt % more alcohol or at least 6 wt % more alcohol, based on total weight of pyrolysis product, than the product produced from the same feedstock pyrolyzed in the absence of a basic metal oxide and a hydrogenation metal catalyst as described herein. In an embodiment, the pyrolysis product can be comprised of at least 1 wt % less ketones and aldehydes, or at least 2 wt % less ketones and aldehydes, or at least 4 wt % less ketones and aldehydes, or at least 6 wt % less ketones and aldehydes, based on total weight of pyrolysis product, than the product produced from the same feedstock pyrolyzed in the absence of a basic metal oxide and a hydrogenation metal catalyst as described herein. It is noted that having, for example, at least 1 wt % less of ketones and aldehydes can correspond to having 1 wt % less of ketones, 1 wt % less of aldehydes, or 1 wt % less of a combination of ketones and aldehydes.

The pyrolysis product according to embodiments of aspects of the present invention can be particularly high in alcohol content. In one embodiment, the pyrolysis product can be comprised of at least 2 wt alcohol, preferably at least 4 wt %, for example at least 6 wt % alcohol, at least 8 wt % alcohol, at least 15 wt % alcohol, or at least 20 wt % alcohol, based on total weight of pyrolysis product.

In a preferred embodiment, the pyrolysis product can comprise from 1 wt % to 50 wt % alcohol, for example from 2 wt % to 25 wt % alcohol or from 5 wt % to 20 wt % to alcohol, based on total weight of pyrolysis product produced.

The pyrolysis product according to aspects of the invention can include any one or more of a wide variety of alcohols. In general, the pyrolysis product can comprise at least one $C_1$-$C_{10}$ alcohol. Exemplary alcohols can include aliphatic, unsaturated, aromatic, linear, branched, and/or cyclic mono-alcohols, diols, triols, and the like, and combinations thereof. Examples of mono-alcohols can include, but are not necessarily limited to, methanol, ethanol, n-propanol, isopropanol, n-butanol, tert-butanol, isobutanol, and the like, and combinations thereof. Examples of diols can include, but are not necessarily limited to, ethylene diol, 1,3-propylene diol, 1,2-propylene diol, 1,4-butanediol, and the like, and combinations thereof. Examples of triols can include, but are not necessarily limited to, glycerol and the like. The pyrolysis product can also advantageously be relatively low in aldehyde content. Preferably, the pyrolysis product can comprise not greater than 20 wt %, for example not greater than 15 wt %, not greater than 10 wt %, or not greater than 5 wt % aldehyde, based on total weight of pyrolysis product.

In addition to an increased alcohol content, the pyrolysis product according to embodiments of the present invention has reduced amounts of carbonyl containing molecules such as aldehydes and ketones. This will be discussed in greater detail in relation to Example 14 below. In one embodiment, the catalyst system described herein having the basic metal oxide and the hydrogenation metal catalyst is included in a pyrolysis system, such as that described above in regards to the FIGURE. As such, the pyrolysis bio-oil, as produced, would have higher levels of alcohol and lower amounts of aldehydes and ketones when compared to a pyrolysis bio-oil produced by a conventional system, or without the catalyst system comprising the basic metal oxide and the hydrogenation metal catalysts. In another embodiment, pyrolysis bio-oil may be conventionally produced, and may then be passed to a separate reactor that has the catalyst system described herein for further processing. This may occur, in one embodiment, prior to the condensation of the bio-oil vapors. This further processing may include the use of the catalyst system comprising the basic metal oxide and the hydrogenation metal catalysts, which would then produce a further processed pyrolysis bio-oil having increased amounts of alcohol, and decreased amounts of carbonyl containing molecules such as aldehydes and ketones, in addition to reduced amounts of unsaturated hydrocarbonaceous compounds.

Even further, the pyrolysis product described in relation to embodiments of the present invention may contain increased amounts of hydrogen. For example, producing a pyrolysis oil in the presence of a catalyst system including a basic metal oxide and a supported hydrogenation metal catalyst can result in the conversion of ketones and aldehydes, such as acetone, acetol, and hydroxyacetaldehyde, to alcohols, such as propane-1,2-diol, ethane-1,2-diol, ethane-1,1-diol, and isopropanol. Conversion of ketones and aldehydes to alcohols results in addition of a $H_2$ molecule to a compound. By increasing the hydrogen content of the oxygenated compounds in the pyrolysis oil, the hydrogen demand required for any future hydroprocessing Or other processing) of the pyrolysis oil can be reduced. As noted above, this additional hydrogen added to the oxygenated compounds is generated in-situ, so that a separate stream of hydrogen does not need to be introduced into the reaction environment to obtain this benefit. Therefore, while the hydrogen would otherwise have been wasted, using embodiments provided herein, the hydrogen, which is produced in-situ, can be utilized to produce a more stable product by reducing aldehyde and ketone levels in the pyrolysis product, such as the pyrolysis bio-oil.

Preferably, at least a portion of the pyrolysis product produced according to aspects of the present invention can be condensed to form a liquid product. The liquid product can advantageously be relatively low in moisture content, relatively low in viscosity, and/or less acidic and corrosive than conventional liquid pyrolysis products.

Any number of chemical compounds can be included in the liquid portion of the recovered pyrolysis product. Typically, this recovered liquid product is called a pyrolysis oil, or a pyrolysis bio-oil. The oil can include one or more of various phenols, cresols, catechols, guaiacol, methyl-substituted phenols, indene, substituted naphthalene, and/or other aromatics.

Char or coke type solids can remain in the reactor or can be filtered from recovered vapor and liquid pyrolysis product portions. In one embodiment, a substantial portion of the products can be steam reformed or partially oxidized to form a synthesis gas or a hydrogen-rich gas.

Overall, potential pyrolysis products may have applications as fuels, adhesives, synthesis gas, phenol formaldehyde resins, phosphate esters, magnetic wire, cleaning and disinfectant compounds, ore floatation, and other applications. The pyrolysis products produced according to aspects of the present invention can advantageously be suitable for use in other applications without the need for extensive secondary processing steps.

In one embodiment of the invention, at least a portion of the pyrolysis product can be hydroprocessed to provide various fuels and chemicals. Hydroprocessing refers to processes or treatments in which at least a portion of the pyrolysis product can be reacted with hydrogen, typically under pressure and in the presence of a hydroprocessing catalyst. Such processes can include, but are not limited to, hydrodeoxygenation, hydrodenitrogenation, hydrodesulfurization, hydrotreating, hydrocracking, hydroisomerization, hydrodewaxing, and the like. For examples of such processes, see U.S. Pat. Nos. 7,513,989, 7,435,335, 7,288,182, 7,288,181, 7,244,352 and 7,220,352. Examples of hydroprocessing can include, but are not limited to, conversion of oxygen-containing hydrocarbons to paraffins.

Additionally or alternately, the present invention can further include the following embodiments.

Embodiment 1

A method of producing an alcohol-containing pyrolysis product, comprising pyrolyzing a hydrocarbon feedstock in the presence of a catalyst system, the catalyst system comprising a basic metal oxide catalyst and a supported hydrogenation metal catalyst to produce a pyrolysis product that contains at least one alcohol, wherein the basic metal oxide catalyst is comprised of at least one metal from Group 2, Group 3 including Lanthanides and Actinides, or Group 4 of the Periodic Table of Elements, and wherein the supported hydrogenation metal catalyst is comprised of at least one metal from Group 6 or Groups 8-10 of the Periodic Table of Elements.

Embodiment 2

The method of Embodiment 1, wherein a hydrogenation metal of the hydrogenation metal catalyst is supported on the basic metal oxide catalyst.

Embodiment 3

The method of Embodiment 1, wherein the catalyst system comprises a mixture of the basic metal oxide catalyst and the supported hydrogenation metal catalyst, the hydrogenation metal catalyst being supported on a refractory oxide support.

Embodiment 4

The method of any of the above embodiments, wherein the hydrocarbon feedstock comprises biomass material.

Embodiment 5

The method of any of the above embodiments, wherein the basic metal oxide catalyst is a Group 2 metal and a hydrogenation metal of the hydrogenation metal catalyst is platinum.

Embodiment 6

The method of any of the above embodiments, wherein a hydrogenation metal of the hydrogenation metal catalyst is one or more of platinum, palladium, nickel, molybdenum, or tungsten.

Embodiment 7

The method of any of the above embodiments, wherein the Group 3 metal comprises at least one of yttrium, cerium, and praseodymium.

Embodiment 8

The method of any of the above embodiments, wherein the Group 2 metal comprises at least one of magnesium or calcium.

Embodiment 9

A method for treating a pyrolysis bio-oil, comprising passing a pyrolysis bio-oil into a reactor comprising a catalyst system, the catalyst system comprising a basic metal oxide catalyst and a supported hydrogenation metal catalyst, to produce a processed pyrolysis bio-oil having reduced quantities of ketones and aldehydes in comparison to the pyrolysis bio-oil.

Embodiment 10

The method of Embodiment 9, further comprising producing the pyrolysis bio-oil by pyrolyzing biomass in the presence of a heat transfer material in a pyrolysis reactor.

Embodiment 11

The method of any of Embodiments 9 or 10, wherein a hydrogenation metal of the hydrogenation metal catalyst is supported on the basic metal oxide catalyst.

Embodiment 12

The method of any of Embodiments 9 or 10, wherein the supported hydrogenation metal catalyst is separate from the basic metal oxide catalyst.

Embodiment 13

The method of any of Embodiments 9-12, wherein the basic metal oxide catalyst is comprised of at least one metal from Group 2, Group 3 including Lanthanides and Actinides, or Group 4 of the Periodic Table of Elements.

Embodiment 14

The method of any of Embodiments 9-13, wherein the hydrogenation metal catalyst is comprised of at least one metal from Group 6 or Groups 8-10 of the Periodic Table of Elements.

Embodiment 15

The method of any of Embodiments 9-14, wherein the basic metal oxide catalyst is a Group 2 metal and the hydrogenation metal catalyst is platinum or palladium.

Embodiment 16

The method of any of Embodiments 9-14, wherein a hydrogenation metal of the hydrogenation metal catalyst is one or more of platinum, palladium, nickel, molybdenum, or tungsten.

Embodiment 17

The method of any of Embodiments 9-14 and 16, wherein the Group 3 metal comprises at least one of yttrium, cerium, and praseodymium.

Embodiment 18

The method of any of Embodiments 9-17, wherein the Group 2 metal comprises at least one of magnesium or calcium.

Embodiment 19

The method of any of Embodiments 9-18, wherein the processed pyrolysis bio-oil further has reduced quantities of unsaturated hydrocarbonaceous compounds in comparison to the pyrolysis bio-oil.

Embodiment 20

The method of any of Embodiments 9-19, wherein the processed pyrolysis bio-oil further has reduced quantities of at least one of acetone, acetol, or hydroxyacetaldehyde.

EXAMPLES

In some of the following examples, the concept of embodiments of the invention is demonstrated by use of both comparative examples and examples based on analogous systems that are not directly related to the invention.

Aspects of the invention were demonstrated using a variety of metal oxides and/or hydrogenation metals as catalysts using a microflow reactor. The microflow reactor consisted of a stainless steel reactor (¼" outer diameter) located in a furnace to which vaporized feed was introduced via a switching valve. The feed used in these experiments was ACS Reagent grade formaldehyde (~37% in water with ~12% methanol as inhibitor) purchased from Sigma-Aldrich, and used as received. The feed was introduced into the vaporizer using a syringe pump. The flowrate of the feed to the reactor was about 25 μL/min and the catalyst load was about 10 mg. The reactor was maintained at a temperature of about 500° C., and the pressure in the reactor was maintained at about 25 psig, conditions typical in a biomass pyrolyzer. Product gases exiting the reactor were collected using a multi-port sampling valve and analyzed using gas chromatography (HP6890 GC using 30 in PLOT-Q column). The HD-insensitive gases in the product (H$_2$, CO, and CO$_2$) were analyzed using an Agilent 3000 Micro GC equipped with a TCD detector.

Analysis of formaldehyde conversion was determined indirectly by measuring the formation of methanol or CO, CO$_2$, and H$_2$ via Equations (1) and (2):

$$2HCHO(g) + H_2O(g) \rightarrow CH_3OH(g) + CO_2(g) + H_2(g) \quad (1)$$

$$2HCHO(g) \rightarrow CH_3OH(g) + CO(g) \quad (2)$$

Equation (1) above provides for the in-situ generation of hydrogen, which, in the presence of a catalytically active hydrogenating metal site, may enable hydrogenation of carbonyl moieties to take place. For example, acetone can be hydrogenated to isopropyl alcohol, as shown below by Equation (3). The H$_2$ as used in Equation (3) below is produced in-situ and in the instance shown below, can be used with a basic metal oxide catalyst and a hydrogenation metal catalyst to convert ketones to unsaturated hydrocarbonaceous compounds.

$$H_3CCOH_3(g) + H_2(g) \rightarrow H_3CCHOHCH_3(g) \quad (3)$$

A correlation of area counts for the methanol peak on the GC with the concentration of methanol in the sample was therefore used as a measure of the amount of methanol formed via the Cannizzaro reaction (Equations 1 and 2) shown above.

Comparative Example 1

In this experiment, the reactor was loaded with about 100 mg of sand. This base case would be equivalent to a standard pyrolyzer in a biomass reactor where hot sand is circulated as the heat transfer medium. Analysis of the reactor effluent showed the methanol concentration to be essentially identical to that of the feed (formaldehyde feed contained ~12% methanol as an inhibitor). Analysis of the gases produced showed about 0.64% $H_2$, about 0.23% CO, and about 0.41% $CO_2$, attributable to decomposition reactions taking on the metal walls of the reactor.

Comparative Example 2

In this experiment, the reactor was loaded with about 90 mg of sand and about 10 mg of Ultrasil™ silica. The silica, was anticipated to be inert for this chemistry. Analysis of the reactor effluent showed the methanol concentration to be essentially identical to that of the feed. Analysis of the gases produced showed about 0.61% $H_2$, about 0.23% CO, and about 0.37% $CO_2$, attributable to decomposition reactions taking on the metal walls of the reactor.

Comparative Example 3

In this experiment, the reactor was loaded with about 90 mg of sand and about 10 mg of ~16% $WO_x/ZrO_2$, a catalyst known to be highly acidic, and therefore not believed to be suitable for the chemistry of aspects of the present invention. Analysis of the reactor effluent showed the methanol concentration to be only about 3% greater than that of the feed. Analysis of the gases produced showed about 0.78% $H_2$, about 0.75% CO, and about 0.54% $CO_2$, attributable to decomposition reactions taking on the metal walls of the reactor, as well as some very minor reaction catalyzed by the acidic metal oxide.

Example 4—In-Situ Hydrogen Production

In this experiment, the reactor was loaded with about 90 mg of sand and about 10 mg of ~12% $CeO_x/ZrO_2$, a catalyst known to be basic. Analysis of the reactor effluent showed the methanol concentration to be about 106% greater than that of the feed. Analysis of the gases produced showed about 8.04% $H_2$, about 8.25% CO, and about 2.38% $CO_2$. This experiment indicated that the basic mixed cerium oxide-zirconium oxide catalyst showed significant activity for the formaldehyde disproportionation reaction.

Example 5—In-Situ Hydrogen Production

In this experiment, the reactor was loaded with about 90 mg of sand and about 10 mg of hydrotalcite, a mineral with nominal composition $Mg_6Al_2(CO_3)(OH)_{16}\cdot 4H_2O$. Upon heating, the hydrotalcite undergoes dehydration and decarboxylation to produce a basic mixed magnesium aluminum oxide. Analysis of the reactor effluent showed the methanol concentration to be about 143% greater than that of the feed. Analysis of the gases produced showed about 3.68% $H_2$, about 3.65% CO, and about 3.87% $CO_2$. This experiment indicated that the basic mixed magnesium aluminum oxide catalyst showed significant activity for the formaldehyde disproportionation reaction.

Example 6—In-Situ Hydrogen Production

In this experiment, the reactor was loaded with about 90 mg of sand and about 10 mg of MgO. Analysis of the reactor effluent showed the methanol concentration to be about 182% greater than that of the feed. Analysis of the gases produced showed about 4.92% $H_2$, about 4.02% CO, and about 3.61% $CO_2$. This experiment indicated that the basic magnesium oxide catalyst showed significant activity for the formaldehyde disproportionation reaction.

Example 7—In-Situ Hydrogen Production

In this experiment, the reactor was loaded with about 90 mg of sand and about 10 mg of $ZrO_2$. Analysis of the reactor effluent showed the methanol concentration to be about 106% greater than that of the feed. Analysis of the gases produced showed about 9.69% $H_2$, about 9.18% CO, and about 2.23% CO. This experiment indicated that the basic zirconium oxide catalyst showed significant activity for the formaldehyde disproportionation reaction.

Example 8—In-Situ Hydrogen Production

In this experiment, the reactor was loaded with about 90 mg of sand and about 10 mg of $Y_2O_3$. Analysis of the reactor effluent showed the methanol concentration to be about 122% greater than that of the feed. Analysis of the gases produced showed about 8.12% $H_2$, about 7.59% CO, and about 2.85% $CO_2$. This experiment indicated that the basic yttrium oxide catalyst showed significant activity for the formaldehyde disproportionation reaction.

Example 9—In-Situ Hydrogen Production

In this experiment, the reactor was loaded with about 90 mg of sand and about 10 mg of $Ce_2O_3$. Analysis of the reactor effluent showed the methanol concentration to be about 76% greater than that of the feed. Analysis of the gases produced showed about 10.45% $H_2$, about 7.95% CO, and about 3.26% $CO_2$. This experiment indicated that the basic cerium oxide catalyst showed significant activity for the formaldehyde disproportionation reaction.

Example 10—In-Situ Hydrogen Production

In this experiment, the reactor was loaded with about 90 mg of sand and about 10 mg of $Pr_2O_3$. Analysis of the reactor effluent showed the methanol concentration to be about 124% greater than that of the feed. Analysis of the gases produced showed about 11.17% $H_2$, about 5.23% CO, and about 5.52% $CO_2$. This experiment indicated that the basic mixed praseodymium oxide catalyst showed significant activity for the formaldehyde disproportionation reaction.

Examples 4-10 demonstrate that solid base catalysts in the form of mixed metal oxides are active for the removal of formaldehyde, as described herein. However, this chemistry is not limited to formaldehyde only, and higher carbon number aldehydes are expected to be removed via crossed Cannizzaro reactions with formaldehyde. An example of this chemistry is shown below in Equation (4) for acetaldehyde:

$$CH_3CHO(g) + HCHO(g) + H_2O(g) \rightarrow C_2H_5OH(g) + CO_2(g) + H_2(g) \quad (4)$$

In this case, acetaldehyde reacts with formaldehyde to produce ethanol and a surface formate which undergoes decomposition to carbon dioxide and hydrogen. Similarly, propionaldehyde will undergo a crossed Cannizzaro reaction with formaldehyde to yield propanol and carbon dioxide and hydrogen.

In the reactions shown in Examples 4-10 above, hydrogen is generated in concentrations ranging from 3.7% to 11.2% for a feed containing ~51% formaldehyde. This hydrogen can thus be used to catalyze hydrogenation reactions using a bifunctional catalyst. An analogous example of this has been demonstrated using methanol conversion chemistry.

Analogous Example 11—Methanol to Olefin Reactions

Analogous Examples 11-13 illustrate the conversion of methanol to olefins using different combinations of catalysts. While the chemistry shown in these examples is different than that used in pyrolysis reactions, these examples do demonstrate the in-situ use of hydrogen for hydrogenation of a feedstock. Conventionally, basic metal oxide catalysts have been used to convert aldehydes to alcohols, which provides a partial cleanup of a feedstock, such as a pyrolysis bio-oil. However, there are other functional groups in pyrolysis bio-oil that may be beneficial to remove, such as ketones and other compounds having unsaturated bonds. These examples are provided to show how in-situ generated hydrogen can be used to perform a traditional hydrogenation activity, such as saturating double bonds.

In this experiment, the reactor was loaded with 50 mg of a SAPO-34 catalyst, known to be catalytically active for the conversion of methanol to light olefins, such as ethylene and propylene. Product gases exiting the reactor were collected and analyzed. Average product selectivities were 1.9% methane, 34.9% ethylene, 0.8% ethane, 38.3% propylene, and 2.5% propane.

Analogous Example 12—Methanol to Olefin Reactions

In this experiment, the reactor was loaded with 50 mg of a SAPO-34 catalyst, upon which 0.1% Pt had been added via impregnation. Product gases exiting the reactor were collected and analyzed. Average product selectivities were 1.5% methane, 34.0% ethylene, 0.98% ethane, 38.7% propylene, and 3.2% propane. Comparison of the results of this experiment to those of the SAPO-34 catalyst without Pt (Example 11 above) indicates that the presence of the Pt on the catalyst has had no impact on the product selectivities due to the absence of hydrogen in the system. As such, while a hydrogenation metal catalyst was used here, there was no hydrogen, such as in-situ hydrogen, available for use.

Analogous Example 13—Methanol to Olefin Reactions

In this experiment, the reactor was loaded with 40 mg of a SAPO-34 catalyst, and 10 mg of La/$ZrO_2$ catalyst upon which 0.1% Pt had been added via impregnation. Product gases exiting the reactor were collected and analyzed. Average product selectivities were 6.3% methane, 0.3% ethylene, 27.8% ethane, 5.4% propylene, and 23.4% propane. Comparison of the results of Example 13 to Example 11 indicates that the presence of the Pt, together with the La/$ZrO_2$, has led to significant hydrogenation of the olefins produced by the SAPO-34 catalyst. It is the basic mixed metal oxide, the La/$ZrO_2$, which is producing the hydrogen via decomposition of the formaldehyde and some methanol in the system. It is believed that formaldehyde forms via reaction of methanol on the steel walls of the reactor. This bifunctional catalyst, Pt on La/$ZrO_2$, is an effective catalyst for the hydrogenation of molecules that can be easily hydrogenated at conditions typical of a biomass pyrolyzer. While this has been demonstrated in this example for the hydrogenation of olefins, it will become apparent to one of ordinary skill in the art based on Example 13 and Example 14 that employing these bifunctional catalysts in a biomass pyrolyzer will generate hydrogen by the decomposition of aldehydes formed in the pyrolysis process which can then be used to catalyze a variety of other chemistries, such as hydrogenation of carboxylic acids to dialcohols and hydrogenation of ketones to alcohols, thereby improving properties of the bio-oil formed.

Example 14

To illustrate the potential benefits of embodiments of this invention, a theoretical calculation of the product distribution resulting from the use of a catalyst according to an aspect of the invention in a pyrolysis reactor is shown in the Table below. The composition of a bio-oil can vary based on the biomass source and processing conditions, so a typical bio-oil composition, as described in "Exploratory Studies of Fast Pyrolysis Oil Upgrading", F. H. Mahfud, Rijksuniversiteit (ironingen, Nov. 16, 2007, ISBN 978-90-367-3226-9) was used as an illustrative example.

TABLE 1

Product distribution resulting from the use of the disclosed catalyst system in a pyrolysis reactor

|  | Comparative Bio-Oil Mass % | Bio-oil with Cannizzaro Mass % | Bio-oil with Cannizzaro and Hydrogenation Mass % |
|---|---|---|---|
| Water | 21.0 | 19.4 | 19.4 |
| Acetone | 4.0 | 4.0 | 2.7 |
| Alcohols |  |  |  |
| Methanol | 2.6 | 3.9 | 3.9 |
| Ethanol | 1.4 | 3.8 | 3.8 |
| Isopropanol | 0.0 | 0.0 | 1.3 |
| Syringols | 5.0 | 5.0 | 5.0 |
| Furans | 6.0 | 6.0 | 6.0 |
| Phenols | 7.0 | 7.0 | 7.0 |
| Sugars | 8.0 | 8.0 | 8.0 |
| Gualacols | 8.0 | 8.0 | 8.0 |
| Aldehydes |  |  |  |
| Formaldehyde | 4.0 | 0.0 | 0.0 |
| Acetaldeyhde | 6.0 | 3.7 | 3.7 |
| Acids |  |  |  |
| Formic | 5.6 | 5.6 | 5.2 |
| Acetic | 8.4 | 8.4 | 8.1 |
| Hydroxyacetaldehyde | 9.1 | 9.1 | 7.3 |
| Acetol | 3.9 | 3.9 | 2.3 |
| Methanediol | 0.0 | 0.0 | 0.4 |
| Ethane-1,1-diol | 0.0 | 0.0 | 0.3 |
| Ethane-1,2-diol | 0.0 | 0.0 | 1.9 |
| Propane-1,2-diol | 0.0 | 0.0 | 1.6 |
| CO | 0.0 | 0.2 | 0.2 |
| CO2 | 0.0 | 3.8 | 3.8 |
| H2 | 0.0 | 0.2 | 0.0 |

As used in Table 1, the column labeled "Comparative Bio-Oil" indicates results for a conventional pyrolysis system, such as without a basic metal oxide catalyst or a hydrogenation metal catalyst. The column labeled "Bio-oil with Cannizzaro" provides results when a basic metal oxide catalyst is utilized by itself. The column labeled "Bio-oil with Cannizzaro and Hydrogenation" provides results when a catalyst system, as described herein, is utilized, such as by using a basic metal oxide catalyst in combination with a hydrogenation metal catalyst.

In determining the composition of the "Bio-oil with Cannizzaro," the following assumptions have been made: 50% of the formaldehyde converts via the reaction of Equation (1), 10% of the formaldehyde converts via the reaction of Equation (2), and the remainder of the formaldehyde converts via a crossed Cannizzaro reaction with acetaldehyde of Equation (4) that consumes 39% of the available acetaldehyde. It has also been assumed that there is no rejection of carbon via decarboxylation reactions, and no decomposition of other oxygenates. Under this reaction scheme, the amount of hydrogen produced is 0.2% by mass of the product which is equivalent to 3.6% by moles of the product.

If a bifunctional catalyst of aspects of this invention is used in the pyrolysis reactor, e.g. the 0.1% Pt on La/ZrO$_2$ described in Example 13, the presence of a hydrogenating functionality will catalyze the conversion of various oxygenated and unsaturated molecules using the hydrogen produced from the Cannizzaro reaction. For illustrative purposes, it can be assumed that all of the available hydrogen is used in the following manner: 25% consumed in hydrogenating acetone, 35% consumed in hydrogenating hydroxyacetaldehyde, 25% consumed in hydrogenating acetol, 10% consumed in hydrogenating formic acid, and 5% consumed in hydrogenating acetic acid. Under these assumptions, the available hydrogen after the Cannizzaro reaction will produce the product distribution shown in the column labeled "Bio-oil with Cannizzaro and Hydrogenation."

Comparing the product produced using the bifunctional catalysts of aspects of this invention to that produced in the absence of any catalyst (Comparative Bio-oil), one can see that there has been a 63% decrease in formaldehyde+acetaldehyde concentration, a 5% decrease in acids, a 20% decrease in hydroxyacetaldehyde, and a 41% decrease in acetol. All of these components are very reactive in the formation of resins, and this decrease in concentration enabled by the catalysts of aspects of this invention will significantly improve the stability of the resulting bio-oil. In addition, this chemistry can result in a 125% increase in the amount of light alcohols produced, such as methanol and ethanol, which are known to stabilize bio-oils.

In particular, Example 14 illustrates various conversions that take place by way of reactions when the catalyst system described herein is utilized in a pyrolysis system. Initially, the mass % of acetone is decreased from 4.0 (using only the basic metal oxide catalyst) to 2.7 (using the basic metal oxide catalyst in combination with the hydrogenation metal catalyst). As shown, acetone is converted to one or more alcohols, such as isopropanol. Further, the mass % of hydroxyacetaldehyde is decreased from 9.1 (using only the basic metal oxide catalyst) to 7.3 (using the basic metal oxide catalyst in combination with the hydrogenation metal catalyst). Hydroxyacetaldehyde is converted to various alcohols. The mass % of acetol is decreased from 3.9 (using only the basic metal oxide catalyst) to 2.3 (using the basic metal oxide catalyst in combination with the hydrogenation metal catalyst). Acetol is converted to one or more alcohols, such as propane-1,2-diol.

This example is illustrative in nature to demonstrate the potential benefits of generating hydrogen in-situ via the Cannizzaro reactions and then using this hydrogen to convert various oxygenated and unsaturated species. Actual conversions of various molecules will depend on the catalyst used, the composition of the reacting stream, and the conditions in the pyrolysis reactor.

The foregoing disclosure provides illustrative embodiments of the invention and is not intended to be limiting. As understood by those of skill in the art, the overall invention, as defined by the claims, encompasses other preferred embodiments not specifically enumerated herein.

What is claimed is:

1. A method of producing an alcohol-containing pyrolysis product, the method comprising:
   pyrolyzing a hydrocarbon feedstock in the presence of a solid heat absorbing material comprising a basic metal oxide catalyst and a supported hydrogenation metal catalyst to produce a pyrolysis product that contains at least one alcohol, wherein the basic metal oxide catalyst comprises at least one metal selected from the group consisting of Group 2, Group 3 including Lanthanides and Actinides, and Group 4 of the Periodic Table of Elements, and wherein the supported hydrogenation metal catalyst comprises at least one metal selected from the group consisting of platinum and palladium;
   wherein the basic metal oxide catalyst and supported hydrogenation metal catalyst comprise about 1-20 wt % of the solid heat absorbing material.

2. The method of claim 1, wherein a hydrogenation metal of the hydrogenation metal catalyst is supported on the basic metal oxide catalyst.

3. The method of claim 1, wherein the hydrogenation metal catalyst is supported on a refractory oxide support.

4. The method of claim 1, wherein the hydrocarbon feedstock comprises biomass material.

5. The method of claim 1, wherein the basic metal oxide catalyst is a Group 2 metal oxide.

6. The method of claim 1, wherein the Group 3 metal comprises at least one of yttrium, cerium, and praseodymium.

7. The method of claim 1, wherein the Group 2 metal comprises at least one of magnesium or calcium.

* * * * *